(12) United States Patent
Richardson et al.

(10) Patent No.: US 6,632,445 B2
(45) Date of Patent: Oct. 14, 2003

(54) UNIT DOSAGE FORMS FOR THE TREATMENT OF HERPES SIMPLEX

(75) Inventors: Kenneth T. Richardson, Anchorage, AK (US); Don C. Pearson, Lakewood, WA (US)

(73) Assignee: ChronoRX, LLC, Anchorage, AK (US)

( * ) Notice: Subject to any disclaimer, the term of this patent is extended or adjusted under 35 U.S.C. 154(b) by 0 days.

(21) Appl. No.: 10/209,432

(22) Filed: Jul. 30, 2002

(65) Prior Publication Data

US 2002/0197313 A1 Dec. 26, 2002

Related U.S. Application Data

(62) Division of application No. 09/828,323, filed on Apr. 5, 2001, now Pat. No. 6,455,061, and a division of application No. 09/396,019, filed on Sep. 15, 1999, now Pat. No. 6,231,889.
(60) Provisional application No. 60/101,308, filed on Sep. 21, 1998.

(51) Int. Cl.$^7$ .......................... A61E 13/00; A61K 31/74; A61K 39/12; A61K 39/245; A61F 2/00
(52) U.S. Cl. ................. 424/422; 424/78.04; 424/204.1; 424/229.1; 424/231.1; 424/427
(58) Field of Search .............................. 424/78.04, 422, 424/427, 204.1, 229.1, 231.1; 514/912, 914, 944, 954

(56) References Cited

U.S. PATENT DOCUMENTS

| | | | |
|---|---|---|---|
| 4,937,234 A | 6/1990 | Fahim | |
| 5,599,719 A | 2/1997 | Woiszwillo et al. | |
| 5,804,594 A | 9/1998 | Murad | |
| 5,962,030 A | 10/1999 | Fine | |
| 6,133,318 A | 10/2000 | Hart | |
| 6,235,756 B1 | 5/2001 | D'Amato | |

OTHER PUBLICATIONS

Terekhina et al.; "Lacrimal and salivary antioxidants in viral infection"; Klin Lab Dagn Jan. 1998; (1):13–15.*
Barnes; "Compatibility of a commercially available low)density polyethylene eye–drop container with antimicrobial preservative and potassium ascorbate"; J Clin Pharm Ther Dec. 1995; 20(6):341–4.*
Angeles Vision Clinic; "Herpes Simplex Keratitis"; http://www.avclinc.com/herpes_simplex.*
Antivial Agents for Ophthalmic Use; http://www.165.229.203.98/aldja/chemotherapy/Antiviral/OPantivir.*
Algert, S.J. et al. "Assessment of dietary intake of lysine and arginine in patients with herpes simplex," *J. Amer. Diet Assoc.* 1987, pp. 1560–1561, vol. 87, No. 11.
Ayala, E. and Krikorian, D. "Effect of L–lysine monohydrochloride on cutaneous herpes simplex virus in the guinea pig,"*J. Med. Virol.* 1989, pp. 16–20, vol. 28.

Eby, G.A. and Halcomb, W.W. "Use of topical zinc to prevent recurrent herpes simplex infection: review of literature and suggested protocols," *Med. Hypotheses* 1985, pp. 157–165, vol. 17.
Kaul, T.N. et al. "Antiviral effect of flavonoids on human viruses," *J. Med. Virol.* 1985, pp. 71–79, vol. 15.
Knowles, R.W. and Person, S. "Effects of 2–deoxyglucose, glucosamine, and mannose on cell fusion and the glycoproteins of herpes simplex virus," *J. Virol.* 1976, pp. 644–651, vol. 18, No. 2.
Kumel, V.G. et al. "[Zinc sulfate and heparin for local therapy of herpes. Antiherpetic drugs, not leading to selection of HSV variants]," *Fortschr. Med.* 1995, pp. 235–238, vol. 113, No. 15.
Martin, C.P. et al. "Antiviral activity of a D–glucosamine derivative against herpetic ulcers (HSV type 2) in rabbit cornea," *Acta. Ophthalmol. (Copenh.)* 1989, pp. 55–60, vol. 67.
Palamara, A.T. et al. "Evidence for antiviral activity of glutathione: in vitro inhibition of herpes simplex virus type 1 replication," *Antiviral Res.* 1995, pp. 237–253, vol. 27.
Ramos–Kuri, M. et al. "Inhibition of three alphaherpesviruses (herpes simplex 1 and 2 and pseudorabies virus) by heparin, heparan and other sulfated polyelectrolytes," *Arch. Med. Res.* 1996, pp. 43–48, vol. 27, No. 1.
Sagripanti, J.L. et al. "Mechanism of copper–mediated inactivation of herpes simplex virus," *Antimicrob. Agents Chemother.* 1997, pp. 812–817, vol. 41, No. 4.
Vossen, R.C. et al. "Intracellular thiol redox status affects rat cytomegalovirus infection of vascular cells," *Virus Res.* 1997, pp. 173–183, vol. 48.
White, L.A. et al. "In vitro effect of ascorbic acid on infectivity of herpesviruses and paramyxoviruses," *J. Clin. Microbiol.* 1986, pp. 527–531, vol. 24, No. 4.

* cited by examiner

Primary Examiner—Thurman K. Page
Assistant Examiner—S. Tran
(74) Attorney, Agent, or Firm—M. Henry Heines; Townsend and Townsend and Crew, LLP

(57) ABSTRACT

The components of this invention are chosen because of their complementarity for the prevention or treatment of diseases caused by the herpes simplex virus. L-Lysine favorably increases the physiologic immunomodulation necessary for defense against this virus. Zinc improves and maintains a normal immune response. 2-Deoxy-2-D-glucose and heparin sodium alter the surface interaction between the herpes virus and the cell, preventing fusion and infectivity. N-Acetyl-L-cysteine increases glutathione levels thereby creating a thiol redox barrier to the virus at the cell membrane. Quercetin reduces intracellular replication of the herpes virus and viral infectivity. Ascorbate, in concert with copper and D-α-tocopherol, provides an antioxidant defense against the herpes virus, which tends to lose latency during period of oxidative, free radical excess. Selenium and quercetin also participate in reducing various oxidative stresses. Together the components of this invention provide the potential for improved resistance to, improved recovery from, and a decreased frequency of recurrence of herpes simplex virus infection.

6 Claims, No Drawings

UNIT DOSAGE FORMS FOR THE TREATMENT OF HERPES SIMPLEX

CROSS REFERENCE TO RELATED APPLICATION

This application is a divisional of Ser. No. 09/828,323, filed Apr. 5, 2001, now U.S. Pat. No. 6,455,061 and is a divisional of Ser. No. 09/396,019, filed Sep. 15, 1999, now U.S. Pat. No. 6,231,889.

This application is related to U.S. Provisional Patent Application No. 60/101,308, filed Sep. 21, 1998, and claims all benefits legally available therefrom. Provisional Patent Application No. 60/101,308 is hereby incorporated by reference for all purposes capable of being served thereby.

BACKGROUND OF THE INVENTION

1. Field of the Invention

This invention is in the field of pharmacology, and relates specifically to the pharmacological treatment of conditions associated with herpes simplex virus infections.

2. Description of the Prior Art

Herpes Simplex—the Virus

No human virus is considered normal flora; although some viruses may be more or less symptomatic, unlike bacteria none can be considered non-pathogenic. And because the viral life cycle is played out within a host cell, the membrane and molecular function of the target eukaryocyte and the biological life cycle of the invasive virion are inextricably entwined.

Viruses may be grouped in a variety of ways; perhaps most simply by considering five elements:

1) Method of entry into the host.
2) Extent of spread in the host.
3) Mode of spread within the host.
4) The host tissue targeted.
5) The fate of the virus after host recovery.

According to this admittedly simple list of characteristics, herpes simplex virus (HSV), Herpesviridae, Simplexvirus, enters the host by direct contact, is spread to a target tissue only, spreads within the host via neuronal axonal flow, targets the dorsal root ganglia and after recovery of the host from an acute infection, remains latent in the targeted tissue.

The HSV virion is a large (100 to 150 m$\gamma$), enveloped virus with an icosahedral capsid. It has double strand DNA with a genome that encodes at least 70 polypeptides—this large amount of regulatory information permits the virus to control its own gene expression and elegantly to modify multiple complex events within the infected cell.

The invading virion binds to host cell receptors. A primary binding site is host cell surface heparan sulfate glycosaminoglycan, which binds with the V3 loop of the viral envelope glycoprotein (gp 120). Another primary binding site may be chondroitin sulfate. Mediated by viral glycoprotein gB and following nonspecific primary binding, more specific binding occurs to the gC4 and gD4 viral surface glycoproteins. The virion envelope fuses with the plasma membrane of the host cell. The capsid is uncoated, the virus invasively inserts surface glycoprotein gB through the host cell plasma membrane and enters the host nucleus where viral DNA is transcribed and processed into mature mRNA; at the same time, host cell mRNA synthesis is inhibited. Invading HSV also inhibits host cell DNA synthesis while viral DNA replicates within the host nucleus. The viral DNA combines with newly formed HSV capsid proteins translated in the cytoplasm, and assembles into progeny virion particles within the nuclear membrane. Concurrent expression of glycoproteins in the host plasma envelope stimulates neighboring cells to clump together. Following cell-to-cell contact by binding and fusion of their respective plasma envelopes, progeny particles invade clumped, neighboring host cells directly or by spread following lysis of previously invaded tissue cells or phagocytes and the process repeats itself.

Viral invasion elicits a phagocytic response coupled with typical phagocytic immune activities—the release of soluble immune mediators (i.e., cytokines) and high respiratory burst responses by activated phagocytes. These immune responses are themselves detrimental to the host; not only because of local tissue necrosis from high environmental levels of free radical release, but also because of the development of mutant, potentially resistant viral strains secondary to toxic local levels of activated oxygen and hydroxyl species.

Herpes Simplex—Clinical Expression

The massive disruption by HSV of host cell molecular functions and of host cellular structure is manifested clinically as host cellular death, resulting in shallow, painful vesicular ectodermal lesions or by hemorrhagic encephalitic necrosis of the brain. Target tissues for HSV are the skin or mucous membranes usually derived from embryonic ectoderm: mouth, skin, vagina, conjunctiva, cornea, etc. The virus enters the host cell by direct mucosal contact or by direct contact of abraded skin. In the skin the virus replicates in epithelial cells and then enters local sensory neurons. The virus travels to the dorsal root ganglia via retrograde axonal flow where it establishes permanent residency. There it establishes latency a state in which the viral lytic genes are silenced and only the latency locus is transcriptionally active. Although latent most of the time, it reactivates intermittently, travels down the sensory nerve and causes vesicular eruptions at or near the site of initial invasion. Alternatively the virus may invade the CNS and cause encephalitis.

The rate of seropositivity to HSV varies widely from country to country: from relatively low in Japan where Herpes simplex Type 1 (HSV-1) seroprevalence for men and women has decreased from 75.3 and 80.6% in 1973 to 54.4 and 59.6%, respectively in 1993 and where Herpes simplex Type 2 (HSV-2) seroprevalence has decreased from 10.2 and 9.9% in 1973 to 1.8 and 1.2%, respectively in 1993, to quite high in Africa where all adult study groups have a high HSV-1 seroprevalence of >80%. HSV infects more than 50% of the adult population, but some infections may be unrecognized. About half of these develop clinical manifestations of the disease. Its most significant manifestations are keratitis, genital lesions and labial vesicular lesions ("cold sores").

HSV-1 typically causes herpes keratitis (cornea). This disease is identified by a typically bizarre dendritic-patterned corneal ulcer that tends to be recurrent and very often leads to scarring with a reduction of vision, sometimes to the level of legal blindness. HSV-1 also causes herpes labialis, peri-orbital, peri-oral, peri-nasal skin eruptions and, in older patients, the virus has been associated with herpes zoster ("shingles") infection of the upper trunk.

HSV-2 causes the most prevalent sexually transmitted disease in the United States and visits to physicians for genital herpes simplex virus infection continue to increase. As many as 30 million Americans are infected with HSV-2. About half of these carriers are symptomatic. The clinical manifestations range from mild genital inflammation to severe, very painful, vesicular lesions and ulceration. Systemic involvement in the most severe cases may include hepatitis. Brain damage and death often are the result of HSV-2 acquired by a newborn infant as it passes through an infected birth canal.

Once the herpes virus (of either kind) has infected the human body, the virus is permanently present. This is particularly true for viral infection of the nerve cells of the dorsal root ganglia that are out of range of the immune system. Less commonly, the epithelial basement membrane may house the latent virus. The virus becomes periodically active when the immune system is depressed or when oxidative stress is increased, i.e., during illness, after exposure to high intensity ultraviolet light, following local tissue trauma, etc.

Although HSV-1 principally causes corneal infections or "cold sores" and HSV-2 most often causes genital herpes, either type can infect the cornea, the mouth and/or the genitals. Similarly although most herpetic ocular infections in adults are caused by HSV-1, other more severe and prolonged cases in adults have been shown to be caused by HSV-2.

Herpes Simplex—Current Clinical Treatment

Present treatment rationales are focused upon preventing the fusion of the virion envelope with the host cell plasma membrane by negatively influencing host cell membrane receptors or by interfering with the glycosylation of viral protein required for fusion, and by reducing viral replication within the host cell nucleus. More recently some attention has been drawn to the relationship between local levels of toxic free radicals and antioxidants in the host target cell environment and apparent target cell resistance to infection following viral reactivation.

A. Ophthalmic Preparations:
1. α-α-α-trifluorothymidine-(Viroptic® 1% solution)—useful in treating HSV-1 and HSV-2 keratoconjunctivitis, i.e., HSV lesions of the conjunctival and corneal epithelium, but not effective in the treatment of associated corneal stromal lesions. It acts by interfering with thymidine synthesis in eukaryocytes, normal or infected. Its precise action against invading viruses is unknown. Little clinical toxicity is described, but pregnant women should use it with caution.
2. 2'-Deoxy-5-idouridine-(Herplex® 0.1% solution)—useful in the treatment of corneal epithelial infection with HSV-1. The delivered solution is converted to idoxuridine which replaces DNA thymidine involved in the enzymatic step of viral replication. The resulting structural faults in viral DNA prevent replicative tissue infection. However, idoxuridine is generally cytotoxic, crosses the placental barrier and is implicated in fetal malformations in rabbits and rats. Pregnant women should use it with caution.
3. 9-β-D-arabinofuranosyladenine-(Vira-A® 3% ointment)—useful in the treatment of corneal epithelial HSV-1 and HSV-2 infections, but not stromal lesions induced by these viruses. Although the mode of action of Vira-A® is not established, it probably acts by interference with viral DNA synthesis. Embryonic mutogenesis has occurred in male germ cells and mouse embryos.

B. Genital Herpes Preparations:
1. acyclovir—(Zovirax® tablets)—useful in the treatment of HSV-1 and HSV-2 as well as other virus infections. Mode of action appears to be interference with viral DNA polymerase resulting in premature termination of the DNA chain and a reduction of viral replication. May be effective in preventing corneal stromal infection if used prophylactically, but expense (A major pharmaceutical wholesale firm, Henry Schein, list prices which range from $2.34 to $4.58 per tablet.), concerns for general cytotoxity and especially the rapid, irreversible development of resistant viral strains, limits this routine use. The use of acyclovir results in the emergence of highly resistant viruses sometimes with only one pass of therapy. Low rates of teratogenicity have been found in rats exposed to acyclovir.

Herpes Simplex—Antiviral Agents Under Study
1. 2-deoxy-D-glucose (glucosamine)—Glycosylation inhibitors such as 2-deoxy-D-glucose have been shown to retard the appearance and speed the evolution of both HSV-1 and HSV-2. There are several steps in the metabolism of virus-induced cellular surface glycoproteins that induce infected cell clumping that may be negatively affected by glucosamine. In similar fashion, by inhibiting glycosylation and thereby reducing levels of surface glycoprotein gD and gB, glucosamine reduces virion-host cell fusion; fusion is inhibited in the presence of reduced levels of viral surface glycoprotein carbohydrate. 2-Deoxy-D-glucose has also been shown to inhibit viral DNA synthesis (human cytomegalovirus) thus reducing viral replication potentials.
2. L-lysine monohydrochloride—Topical application of L-lysine to the skin of guinea pigs protected the skin from HSV inoculation. It is suggested that LMH exerts an immuno-modulatory effect in the herpes simplex host. More specifically, a study involving 52 subjects indicates that oral LMH is an effective agent for the reduction of occurrence, severity and healing time for herpes simplex virus infections. One study reported that subjective improvement seemed to occur in 88% of herpes simplex patients using L-lysine. However, there are studies in which L-lysine is reported to be ineffective with daily dosages below about 1000 milligrams per day. At least one study found that L-lysine had no effect on the rate of healing or the appearance of lesions. The conflicting results obtained for the efficacy of lysine for herpes infections may be explained by:
   1) the great variability of the relative amounts of lysine and arginine in diets; and
   2) failure to measure the serum lysine concentration. (The latter should be maintained above 165 nmol/mL)

The higher the arginine/lysine ratio in any diet, the greater the risk for herpes recurrence. Patients with diets high in naturally occurring arginine, such as legumes, whole grains, and nuts, are more vulnerable to herpes simplex recurrence than those whose diets are high in lysine, such as meat and dairy products. The mean daily intakes of lysine and arginine for 16 persons studied were 8.11 g±2.28 and 6.32 g±1.74, respectively. The standard deviations from the mean intake levels are notably wide and most likely illustrate the large variability of lysine and arginine intake in individual diets. This widely variable dietary intake underlines the value of dietary supplementation in countering herpes simplex virus infections; a better dietary balance between these two amino acids should help reduce the existing statistical difference in herpes recurrence.

3. Glutathione (GSH) and Selenium ($Se^{2+}$)—In vitro studies show that intracellular, endogenous, reduced GSH levels are significantly and immediately decreased in the first 24 hours after herpes virus invasion. This dramatic cellular depletion emphasizes the importance of GSH in the host cell's defense against the virus. Supplementation with exogenous GSH not only restored intracellular levels almost to those found in uninfected cells, but also inhibited over 99% of the replication of HSV-1. Although, GSH interferes with the late replication stages of the HSV-1 cycle, it does not disturb normal cellular metabolism.

Human GSH levels cannot be raised directly by supplemental administration in the diet. GSH is produced intracellularly from precursor amino acids including glycine and cysteine. One GSH precursor, N-acetyl-L-cysteine (NAC)—a high endogenous thiol in redox status—has itself been found to possess antiviral antioxidative effectiveness. This study suggested that a high thiol redox status may contribute to the apparent barrier function of endothelial cells with respect to viral infection (in this case, cytomegalovirus) and that oxidative stress may facilitate infection of the vascular wall. In fact, the activity of antioxidants such as glutathione reductase, glutathione peroxidase and Cu—Zn superoxide dismutase appear to be reduced in the lacrimal fluid of patients with herpes simplex keratitis and are altered during the active phase of the disease. Impaired inhibition of the hydroxyl radical and a drop of antioxidant activities in herpes-infected cornea and tears appear to be factors in the pathogenesis of ophthalmic herpes. The trace element $Zn^{2+}$, plays an important, if indirect, role here because it function as a cofactor for the $Se^{2+}$-dependent protective enzyme glutathione peroxidase.

4. Quercetin—In an in vitro cell culture study, the naturally occurring flavanol 3,3',4',5,7-pentahydroxyflavone (quercetin) caused a concentration-dependent reduction of infectivity of a number of viruses, including HSV-1. In addition, it reduced intracellular viral replication. This activity may be related to the ability of quercetin to increase non-protein —SH compounds (important anti-oxidant agents) and increase glutathione peroxidase activity. Yield reduction studies (chick embryo fibroblasts) reveal that quercetin acts synergistically with acyclovir and with 5-ethyl-2'-deoxyuridine to enhance the HSV-1 and HSV-2 antiviral activity of these widely used clinically pharmaceuticals.

5. Ascorbate, ascorbic acid and Copper ($Cu^{2+}$)—Impaired inhibition of hydroxyl radicals and reduced levels of ascorbic acid in the corneae and tears of herpes-infected eyes are factors in the pathogenesis of ophthalmic herpes. Suspensions of HSV have been inactivated by copper-catalyzed sodium ascorbate. Although inactivation of herpes simplex virus can be achieved by $Cu^{2+}$ used alone, this effect is enhanced by the addition of ascorbate. One study mentions that a topical paste consisting solely of vitamin C was effective in the treatment of HSV lesions.

6. Zinc ($Zn^{2+}$)—Zinc sulfate inactivates free herpes simplex virus. $Zn^{2+}$ inactivation of the virus lessens after several passes, but this partial resistance of the virus eventually disappears. (In contrast, resistance to acyclovir is complete and irreversible after a single pass.) Consistent with this in vitro evidence of the persistence of zinc's inhibitory effect on HSV, is the finding that long-term, topical application of $Zn^{2+}$ greatly reduces or eliminates recurrences of genital herpes. Even low concentrations of zinc, prevented recurrent herpes simplex. These direct contact effects of zinc on HSV reflect and complement the systemic importance of $Zn^{2+}$ in global immune system maintenance. For example: in rabbits $Zn^{2+}$ plays a vital role in maintaining immunocompetence. Humoral and cellular immunity are depressed in the $Zn^{2+}$-deficient rabbit. Epithelial and stromal HSV keratitis are more severe in the $Zn^{2+}$-deficient rabbit and these conditions are not improved by local $Zn^{2+}$ replacement used alone (zinc sulfate ointment). This treatment failure highlights the necessity of maintaining a healthy underlying immune system in resisting HSV and the important involvement of dietary $Zn^{2+}$ in maintaining that immunity.

7. Magnesium ($Mg^{+2}$)—The recommended daily allowance of ionic $Mg^{+2}$ for humans is 350 mg. $Mg^{+2}$ deficiencies have been documented in many segments of the world population. It is estimated that the average adult in Western society has a dietary magnesium shortfall of 90–178 mg per day. $Mg^{+2}$ deficiencies are particularly prevalent among diabetics with normal renal function, alcoholics, smokers, the elderly, and those who suffer from a variety of gastrointestinal mobility disorders.

Ionic $Mg^{+2}$ in mammals resides in three compartments: (1) in bone; (2) in an intracellular bound form or in an intracellular unbound form; and (3) in circulating bound and unbound forms. When the concentration of circulating $Mg^{+2}$ in the bloodstream increases as a result of the dietary uptake of $Mg^{+2}$, the body quickly responds by sequestering the $Mg^{+2}$ into one of the bound or intracellular forms listed above. If elemental $Mg^{+2}$ is ingested in a bulk amount that results in the absorption of a $Mg^{+2}$ bolus in excess of 8 mEq, the renal excretion of $Mg^{+2}$ rapidly increases and, as a result, becomes less efficient in the resorption of this element. Thus the accurate sustenance of an appropriate $Mg^{+2}$ level requires the repeated administration of carefully designed $Mg^{+2}$-containing medicaments with correctly formulated, absorption targeted amounts.

Among other functions, $Mg^{+2}$ and $Cu^{+2}$ deficiencies impair antioxidant defenses through decreased synthesis of GSH and reduced activity of CuZn superoxide dismutase, respectively. $Mg^{+2}$ deficiencies enhance general oxidative stress levels by permitting elevated circulating levels of factors that promote free radical generation and which are mitogenic. This results in increased tissue necrosis in the presence of acute local levels of active oxygen species or hydroxyl radicals.

7. Heparin Sodium—Heparan sulfate is a primary receptor for viral fusion with the host cell. Very low doses of sodium heparin bind competitively with host cell surface heparan sulfate receptors and thus inhibit the very earliest stages of virion fusion. In addition, heparin sodium mobilizes fibroblastic growth factor (bFGF) by releasing it from its bound status to heparan sulfate. bFGF is a potent mediator of inflammatory angiogenesis fundamental to lesion repair. The effective doses of heparin sodium required for these activities are greatly lower than those necessary for anticoagulant purposes.

SUMMARY OF THE INVENTION

Although several in vitro and in vivo studies appear to support the antiviral effectiveness of individual biofactors, almost universally the studies focus upon attempts to measure the effect of the application of single biofactors, i.e., the effectiveness of each biofactor used independently as measured against a single physiological endpoint.

The invention resides in a unique, orchestrated pharmaceutical formulation for use in the treatment of HSV-1 and HSV-2 that takes advantage of the additive and synergistic antiviral complementarity of these biofactors in a variety of applications and makes these specific formulations available in a variety of dosage forms.

The present treatment of HSV infected or exposed patients with cytotoxic drugs is imprecisely effective—i.e., 1) While these drugs may be clinically effective in reducing active epithelial disease they are not effective in treating corneal stromal disease. 2) For a variety of reasons it is not presently practical to treat patients prophylactically between recrudescent episodes of viral activity. Furthermore, current treatment is expensive and involves the use of admittedly cytotoxic agents. In a broader failure, current treatment programs focus almost exclusively upon the topical treatment of acutely infected tissue while ignoring the global, complex, metabolic and immunological cellular environment within which the disease process operates.

This invention takes a different approach entirely. By combining a variety of agents that have been shown individually to have antiviral activity at a variety of the required nodal steps in the invasive interplay between the HSV virion and the host cell, this invention addresses the more expansive physiological stage upon which this pathological activity occurs. Furthermore, the agents used in the invention have not been shown to have any cytotoxicity when used in appropriate dose levels, they are inexpensive and can be used prophylactically without concern for any significant development of viral resistance. Unlike current treatment methods the invention will be effective against stromal HSV infection and will reduce viral rates of recurrence. The invention will not replace current therapy for active HSV infection. It will, however, reduce clinical requirements for present therapies by minimizing therapeutic failure, thus reducing morbidity and recrudescence.

The combined complementary activities of the elements of the invention reduce HSV infection by:

1. Retarding infected host cell clumping by reducing surface glycoprotein.

This reduction of cell clumping mechanically interferes with virion-host cell fusion and interferes with cell-to-cell spread. (2-deoxy-D-glucose)

2. Retarding virion-host cell fusion physiologically by reducing levels of glycoprotein gB carbohydrate and, thus, reducing virus infectivity. (2-deoxy-D-glucose)
3. Modifying the host-cell immunomodulation abilities and thus improving existing statistical differences in herpes recurrence rates between patients with dietary L-arginine/L-lysine imbalances. (L-lysine)
4. Improving host-cell defenses by increasing endogenous reduced-GSH levels. Maintenance of GSH levels interferes with late-stage replication of HSV-1. ($Se^{2+}$, NAC)
5. Improving local host-cell antiviral antioxidative effectiveness by reducing local levels of hydroxyl radicals involved in the pathogenesis of ophthalmic herpes. This improves local tissue survival by countering high levels of free radical damage. ($Se^{2+}$)
6. Increasing host-cell levels of antioxidant thiols and glutathione peroxidase and, in addition, providing synergistic anti-replicative activity in conjunction with acyclovir and deoxyuridine. (quercetin, NAC)
7. Inactivating viral replication and reducing host-cell levels of hydroxyl radicals. ($Cu^{2+}$, ascorbate—alone or, more effectively, in combination)
8. Locally inactivating HSV without creating long-term resistance and concurrently ensuring adequate immune system stability. ($Zn^{2+}$)
9. Inhibiting primary virus fusion by blocking access to the heparan sulfate receptor and improving lesion healing by stimulating bFGF mediated reparative angiogenesis. (heparin sodium)
10. Inhibiting viral DNA synthesis and thus reducing viral replication. (2-deoxy-D-glucose)

In vitro studies or limited clinical evaluations have shown each of these biofactors to have some antiviral activity when used alone. They have not before been united in appropriately designed multi-factor formulations available in a variety of delivery vehicles or modes. The invention is unique in providing this new, safe, effective and inexpensive addition to current therapeutic options, thereby improving the potential for success in treating a worldwide disease with severe morbidity, and in neonates, severe mortality potential.

DETAILED DESCRIPTION OF THE INVENTION AND PREFERRED EMBODIMENTS

Definitions

All terms appearing in this specification and the appended claims are used in the same manner as commonly recognized among those skilled in the technology and terminology of pharmacology. These terms are therefore used in accordance with their conventional definitions, except as otherwise noted. Further clarifications of some of these terms as they apply specifically to this invention are offered below.

"Unit dosage form" refers to a composition intended for a single administration to treat a subject suffering from a disease or medical condition. Each unit dosage form typically comprises each of the active ingredients of this invention plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

An "active agent" or "active ingredient" is a component of a dosage form that performs a biological function when administered or induces or affects (enhances or inhibits) a physiological process in some manner. "Activity" is the ability to perform the function, or to induce or affect the process. Active agents and ingredients are distinguishable from excipients such as carriers, vehicles, diluents, lubricants, binders, buffers and other formulating aids, and encapsulating or otherwise protective components.

"Delivery vehicle" is a composition, which comprises one or more active agents, and is designed to release the active agent in a particular fashion, either by immediately dispersing the agents, or by releasing the agents in a slow sustained fashion. The term encompasses porous microspheres, microcapsules, cross-linked porous beads, and liposomes that contain one or more active ingredients sequestered within internal cavities or porous spaces. The term also includes osmotic delivery systems, coated tablets or capsules that include nonporous microspheres, microcapsules, and liposomes, and active agents dispersed within polymeric matrices. A dosage form can include one or more delivery vehicles.

"Controlled" or "sustained" or "time release" delivery are equivalent terms that describe the type of active agent delivery that occurs when the active agent is released from a delivery vehicle at an ascertainable and manipulatable rate over a period of time, which is generally on the order of minutes, hours or days, typically ranging from about thirty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract.

"Targeted" or "site-specific" delivery means that the pharmaceutical preparation is formulated to limit the release of its contents in an amount appropriate to the site where release occurs. The term refers in particular to the active agent, whose site-specific delivery implements the performance of the therapeutic function at a specific site within the body of the subject to whom the preparation is administered.

The phrase "therapeutically effective amount" means an amount sufficient to produce a therapeutic result. Generally the therapeutic result is an objective or subjective improvement of a disease or condition, achieved by inducing or enhancing a physiological process, blocking or inhibiting a physiological process, or in general terms performing a biological function that helps in or contributes to the elimination or abatement of the disease or condition.

The phrase "substantially homogeneous," when used to describe a formulation (or portion of a formulation) that contains a combination of components, means that the components, although each may be in particle or powder form, are fully mixed so that the individual components are not divided into discrete layers or form concentration gradients within the formulation.

Composition, Formulations and Dosages

A: Oral Dosage Forms

The amounts of the eight primary components of the oral dosage form of the pharmaceutical preparation of this invention can vary, although in preferred preparations the components are present in amounts lying within certain ranges. Expressed in terms of milligrams the components and their preferred ranges may be as follows:

in the range of about 32 mg to about 1610 mg, magnesium oxide in the range of about 50 mg to abut 1600 mg.

For N-acetyl-L-cysteine in Table I, L-2-oxothiazolidine-4-carboxylate may be substituted in the range of about 80 mg to about 4000 mg.

For zinc picolinate in Table I, the following may be substituted: zinc sulfate in the range of about 3.7 mg to about 198 mg, zinc dinicotinate in the range of about 7.1 mg to about 380 mg, zinc ascorbate in the range of about 9.5 mg to about 500 mg, zinc L-acetylcysteinate in the range of about 9 mg to about 480 mg, zinc L-lysinate in the range of about 8 mg to about 435 mg.

For copper sulfate in Table I, the following may be substituted: copper L-acetylcysteinate in the range of about 1 mg to about 30 mg.

A slower, more sustained release of the active agents can be achieved by placing the active agents in one or more delivery vehicles that inherently retard the release rate. Examples of such delivery vehicles are polymeric matrices that maintain their structural integrity for a period of time prior to dissolving, or that resist dissolving in the stomach but are readily made available in the post-gastric environment by the alkalinity of the intestine, or by the action of metabolites and enzymes that are present only in the intestine. The preparation and use of polymeric matrices designed for sustained drug release is well known. Examples are disclosed in U.S. Pat. No. 5,238,714 (Aug. 24, 1993) to Wallace et al.; Bechtel, W., Radiology 161: 601–604 (1986); and Tice et al., EPO 0302582, Feb. 8, 1989. Selection of the most appropriate polymeric matrix for a particular formulation can be governed by the intended use of the formulation. Preferred polymeric matrices are hydrophilic, water-swellable polymers such as hydroxymethylcellulose, hydroxypropylcellulose, hydroxyethylcellulose, hydroxymethylpropylcellulose, polyethylene oxide, and porous bioerodible particles prepared from alginate and chitosan that have been ionically crosslinked.

A delayed, post-gastric, prolonged release of the active ingredients in the small intestine (duodenum, ileum, jejunum) can also be achieved by encasing the active agents, or by encasing hydrophilic, water-swellable polymers containing the active agents, in an enteric (acid-resistant) film.

TABLE I

| Component | Dosage in milligrams | | % in bi-layered | |
|---|---|---|---|---|
| | Preferred | Most Preferred | Immed. | Sustain. |
| 2-amino-2-deoxy-D-glucose | 75 to 2500 | 250 to 1500 | 40–60% | balance |
| L-lysine monohydrochloride | 150 to 5000 | 500 to 20000 | 40–60% | balance |
| N-acetyl-L-cysteine | 80 to 4000 | 200 to 1200 | 40–60% | balance |
| L-selenomethionine | 0.05 to 1.0 | 0.124 to 0.500 | 100% | |
| D-alpha-tocopherol | 15 to 1600 | 50 to 800 | 40–60% | balance |
| Quercetin | 6.0 to 300 | 20 to 120 | 40–60% | balance |
| Magnesium ascorbate | 80 to 3300 | 270 to 1350 | 40–60% | balance |
| Copper sulfate | 0.4 to 14 | 1.0 to 8.0 | 100% | |
| Zinc picolinate | 7.0 to 380 | 24 to 150 | 40–60% | balance |

For magnesium ascorbate in Table I, the following may be substituted: magnesium L-acetylcysteinate in the range of about 80 mg to about 3300 mg, magnesium 2,N-thioctylcysteinate in the range of about 56 mg to about 2800 mg, magnesium 2,N-thioctyltaurate in the range of about 50 mg to about 2500 mg, magnesium taurate in the range of about 80 mg to about 3400 mg, magnesium acetate in the range of about 175 mg to about 5800 mg, magnesium citrate One class of acid-resistant agents suitable for this purpose is that disclosed in Eury et al., U.S. Pat. No. 5,316,774 ("Blocked Polymeric Particles Having Internal Pore Networks for Delivering Active Substances to Selected Environments"). The formulations disclosed in this patent consist of porous particles whose pores contain an active ingredient and a polymer acting as a blocking agent that degrades and releases the active ingredient upon exposure to either low or high pH or to changes in ionic strength. The most effective enteric materials include polyacids having a $pK_a$ of from about 3 to 5. Examples of such materials are fatty acid mixtures, methacrylic acid polymers and copolymers, ethyl cellulose, and cellulose acetate phthalates. Specific examples are methacrylic acid copolymers sold under the name EUDRAGIT®, available from Rohm Tech, Inc., Maiden, Mass., USA; and the cellulose acetate phthalate latex AQUATERIC®, available from FMC Corporation, New York, N.Y., USA, and similar products available from Eastman-Kodak Co., Rochester, N.Y., USA.

Acid-resistant films of these types are particularly useful in confining the release of components post-gastric environment. Acid-resistant films can be applied as coatings over individual particles of the components of the formulation, with the coated particles then optionally compressed into tablets. An acid-resistant film can also be applied as a layer encasing an entire tablet or a portion of a tablet where each tablet is a single unit dosage form.

The oral dosage forms of the invention optionally include one or more suitable and pharmaceutically acceptable excipients, such as ethyl cellulose, cellulose acetate phthalates, mannitol, lactose, starch, magnesium stearate, sodium saccharin, talcum, glucose, sucrose, carbonate, and the like. These excipients serve a variety of functions, as indicated above, as carriers, vehicles, diluents, binders, and other formulating aids. In general, the dosage forms of this invention include powders, liquid forms, tablets or capsules.

In certain embodiments of the invention, the oral dosage form is a substantially homogeneous single layer tablet that releases all of its components into the stomach upon ingestion. In certain other embodiments of the invention, the oral dosage form is a combination tablet in which the components are divided into two portions: one that is fully released into the stomach upon ingestion, and the other protected by an acid-resistant coating for release only in the intestine, and optionally in a sustained-release manner over a period of time The oral dosage forms of this invention can be formulated for administration at rates of either one unit dosage form per day, or two or more. Unit dosage forms to be taken two to four times per day are preferred.

Examples 1 through 7 are offered for purposes of illustration only.

EXAMPLE 1

A single layer tablet, substantially homogeneous in composition, which will disintegrate upon ingestion to provide simultaneous accessibility to all components, is prepared with the following composition:

TABLE II

|  | Weight % | Weight (mg) |
| --- | --- | --- |
| Components |  |  |
| Magnesium L-Ascorbate | 11.45% | 427.76 |
| L-Selenomethionine | 0.002% | 0.08 |
| L-Lysine monohydrochloride | 32.11% | 1200.00 |
| Copper sulfate | 0.07% | 2.51 |
| Zinc Picolinate | 3.84% | 143.37 |
| 2-Amino-2-deoxy-D-glucose | 6.02% | 225.00 |
| N-Acetyl-L-cysteine | 18.73% | 700.00 |
| Quercetin | 1.87% | 70.00 |
| Excipients |  |  |
| Magnesium Stearate | 0.75% | 28.15 |
| Starch | 25.15% | 940.00 |

The tablet is coated with a coating that dissolves in an aqueous environment. Examples of such a coating are SURELEASE and OPADRY (both available from Colorcon, West Point, Pa., USA).

The tablet is made by weighing and mixing all ingredients together in a twin-shell blender, granulating either by roller compaction and milling or by a wet granulation process, and feeding the mixture into a high-speed, rotary tablet press. The starch is a tablet binder, for which lactose can be substituted if desired.

EXAMPLE 2

This example illustrates a dual layer tablet, with each layer substantially homogeneous in composition, including an immediate release layer that disintegrates in the stomach to provide simultaneous accessibility to all of the immediate release components and a controlled release layer that remains intact until reaching the intestine where it provides accessibility to all of its components. The tablet is prepared with the following composition:

TABLE III

|  | Weight % | Weight (mg) |
| --- | --- | --- |
| BI-LAYER TABLET 49% CONTROLLED RELEASE |  |  |
| Components |  |  |
| Magnesium L-Ascorbate | 11.1% | 213.88 |
| L-α-Tocopherol | 8.2% | 157.58 |
| L-lysine monohydrochloride | 28.5% | 550.00 |
| 2-amino-2-deoxy-D-glucose | 7.8% | 150.00 |
| N-Acetyl-L-Cysteine | 15.5% | 300.00 |
| Quercetin | 1.8% | 35.00 |
| Excipients |  |  |
| Magnesium Stearate | 0.81% | 15.6 |
| Polymer (H2O Sol, Cellulose) | 26.40% | 510 |
| ACID RESISTANT FILM 51% IMMEDIATE RELEASE |  |  |
| Components |  |  |
| Magnesium L-Ascorbate | 10.7% | 213.88 |
| L-Selenomethionine | 0.004% | 0.08 |
| D/L α-Tocopherol | 7.9% | 157.58 |
| L-Lysine | 27.6% | 550.00 |
| Copper sulfate | 0.2% | 4.40 |
| Zinc Picolinate | 4.3% | 86.02 |
| 2-amino-2-deoxy-D-glucose | 7.5% | 150.00 |
| N-Acetyl-L-Cysteine | 12.6% | 250.00 |
| Quercetin | 1.9% | 37.00 |
| Excipients |  |  |
| Magnesium Stearate | 0.79% | 15.64 |
| Starch | 26.4% | 525.00 |
| AQUEOUS FILM |  |  |

The controlled release layer comprises 49% by weight of the tablet and has an acid-resistant coating separating it from the immediate release layer. The immediate release layer comprises 51% by weight of the tablet and has a coating that dissolves in an aqueous environment.

Ingredients for each layer are fed into appropriate hoppers of a two-layer, rotary tablet press, and compressed into two-layer tablets. The magnesium stearate present in both layers provides lubrication of the tablet press and serves as a minimal source of magnesium in the formulation. Selenium may be added as a spray.

Upon oral ingestion of the tablet, agents of the immediate release layer dissolve rapidly in the stomach and are available for immediate absorption in the gastrointestinal tract. The polymer matrix of the controlled release layer, having been given an enteric coating in the granulation process with EUDRAGIT, does not dissolve in the acid pH of the stomach, but remains intact until it passes to the upper part of the small intestine, where the enteric coating dissolves in the more alkaline environment of the intestine. The polymeric matrix then immediately begins to imbibe water from the intestinal fluid, forming a water-swollen gel. The agents incorporated into this layer are then available for intestinal absorption as they osmotically diffuse from the gel. Since the agents have been selected with a view toward their water solubilities, the rate of diffusion of each agent is reasonably constant for the useful life of the matrix (approximately four hours), by which time the incorporated agents are finally depleted and the matrix disintegrates.

B. Ophthalmic Dosage Forms

The ophthalmic dosage forms include solutions and suspensions prepared for use as eye drops to provide immediate therapeutic levels of the formulation and ophthalmic ointments designed to provide slower release rates or for use at bedtime.

Ophthalmic dosage forms in accordance with this invention contain the following active ingredients: ascorbic acid, at a preferred concentration of from about 1.3 $\mu$g/mL to about 30 $\mu$g/mL; 2-amino-2-deoxy-D-glucose, at a preferred concentration of from about 0.01 $\mu$g/mL to about 0.2 $\mu$g/mL; zinc sulfate, at a preferred concentration of from about 0.06 $\mu$g/mL to about 8.5 $\mu$g/mL; and L-lysine hydrochloride, at a preferred concentration of from about 1.6 $\mu$g/mL to about 23 $\mu$g/mL. Ophthalmic eyedrop dosage forms of this invention preferably also contain copper sulfate in a concentration ranging from about 0.4 $\mu$g/mL to about 15 $\mu$g/mL. In further preferred ophthalmic eyedrop dosage forms of this invention, heparin sodium is present in a concentration ranging from about 0.6 units/mL. In still further preferred ophthalmic eyedrop dosage forms of this invention, N-acetyl-L-cysteine is present in a concentration ranging from about 0.02 mg/mL to about 0.5 mg/mL. In ophthalmic ointment or gel dosage forms of this invention, copper sulfate is preferably present at a concentration of from about 0.4 $\mu$g/mL to about 15 $\mu$g/mL. In further preferred ophthalmic ointment or gel dosage forms of this invention, quercetin is preferably present at a concentration of from about 0.12 $\mu$g/mL to about 2.75 $\mu$g/mL. In further preferred ophthalmic ointment or gel dosage forms of this invention, heparin sodium is preferably present at a concentration of from about 0.6 units/mL to about 8 units/mL. In still further preferred ophthalmic ointment or gel dosage forms of this invention, N-acetyl-L-cysteine is preferably present at a concentration of from about 0.2 units/mL to about 0.5 units/mL.

EXAMPLE 3

1. Eye drop—The eye drop dosage form of the invention will optionally include one or more suitable and pharmaceutically acceptable inactive excipients, including but not limited to: preservatives from a group including benzalkonium chloride, methylparaben, edetate disodium, thimersol, chlorbutanol; buffers from a group including sodium citrate, potassium chloride, magnesium chloride, sodium acetate, citric acid, sodium lactate; vehicles from a group including polyvinyl alcohol, hydroxy methylcellulose, cetyl alcohol, carboxymethylcellulose, hydroxy-propylenemethyl cellulose; pH adjusters from a group including sulfuric acid, hydrochloric acid, sodium hydroxide, monosodium or disodium phosphate; purified water USP; poloxamer 407 or 188, polysorbate 80; polyoxyethylene polyoxypropylene compound; mineral oil USP and similar products.

The above inactive excipients serve a variety of functions as carriers, vehicles, diluents, binders, preservatives, buffers, pH adjusters, emulsifiers and other formulating aids as briefly listed above and are currently in wide use in ophthalmic pharmaceutical products manufactured under GMP standards.

The eye drop dosage form of this invention can be formulated for administration at a rate of one unit dosage form daily or two or more unit dosage forms four times daily. A unit dosage form taken three to four times per day is preferred.

The amounts of the seven primary components of the eye drop dosage form of this invention can vary, although in preferred preparations the components are present in amounts lying within certain ranges.

A solution for use as an eye drop for delivering all components simultaneously, is prepared with the following composition:

TABLE IV

Ophthalmic Solution

| Components | |
|---|---|
| Ascorbic acid | 0.64% |
| L-lysine hydrochloride | 0.60% |
| Zinc Sulfate | 0.04% |
| Copper Sulfate | 0.06% |
| N-Acetyl-L-cysteine | 0.60% |
| 2-Amino-2-deoxy-D-glucose | 0.38% |
| | USP units/mL |
| Heparin sodium | 1.60 |
| Excipients | |
| Polyvinyl alcohol, sulfated | 1.00% |
| Polyethylene glycol | 0.50% |
| Benzalkonium chloride | 0.004% |

EXAMPLE 4

2. Ointment—An ophthalmic ointment dosage form for more prolonged delivery of the formulation or for use at bedtime will optionally include one or more suitable and pharmaceutically acceptable inactive excipients, including but not limited to: chlorbutanol, polyethylene mineral oil gel, white petrolatum USP, mineral oil USP, petrolatum and lanolin alcohol, purified water USP, polyvinyl alcohol gel and similar products.

The above excipients serve a variety of functions as carriers, vehicles, diluents, binders, preservatives, buffers, pH adjusters, emulsifiers and other formulating aids and are currently in wide use in pharmaceutical products manufactured under GMP standards.

The ointment dosage forms of this invention can be formulated for administration at rates of one unit dosage form daily or two or more unit dosage forms four times daily. Unit dosage forms to be used one time per day at bedtime or three times per day are preferred.

The amounts of the eight primary components of the ophthalmic ointment dosage form of this invention can vary, although in preferred preparations the components are present in amounts lying within certain ranges.

TABLE V

Ophthalmic Ointment

| Components | |
|---|---|
| Ascorbic acid | 0.80% |
| L-lysine hydrochloride | 0.74% |
| Zinc Sulfate | 0.05% |
| Copper Sulfate | 0.08% |
| N-Acetyl-L-cysteine | 0.75% |
| 2-Amino-2-deoxy-D-glucose | 0.48% |
| Quercetin | 0.24% |
| | USP units/mL |
| Heparin sodium | 2.00 |
| Excipients | |
| Polyvinyl alcohol, sulfated | 0.05% |
| Mineral oil | 30% |
| White petrolatum | 45% |

EXAMPLE 5

C. Buccal Mucosal Dosage Forms

This dosage form includes solutions and suspensions prepared for use for application to the buccal mucosa to provide immediate therapeutic levels of the formulation.

The buccal mucosa dosage form of the invention will optionally include one or more suitable and pharmaceutically acceptable inactive excipients, including but not limited to: preservatives from a group including benzalkonium chloride, methylparaben, edetate disodium, thimersol, chlorbutanol; buffers from a group including sodium citrate, potassium chloride, magnesium chloride, sodium acetate, citric acid, sodium lactate; vehicles from a group including polyvinyl alcohol, hydroxy methylcellulose, cetyl alcohol, carboxymethylcellulose, hydroxy-propylenemethyl cellulose; pH adjusters from a group including sulfuric acid, hydrochloric acid, sodium hydroxide, monosodium or disodium phosphate; purified water USP; poloxamer 407 or 188, polysorbate 80; polyoxyethylene polyoxypropylene compound; mineral oil USP and similar products.

The above inactive excipients serve a variety of functions as carriers, vehicles, diluents, binders, preservatives, buffers, pH adjusters, emulsifiers and other formulating aids as briefly listed above and are currently in wide use in pharmaceutical products manufactured under GMP standards.

The buccal mucosa dosage form of this invention can be formulated for administration at a rate of one unit dosage form daily or two or more unit dosage forms four times daily. A unit dosage form taken three to four times per day is preferred.

The amounts of the seven primary components of the buccal mucosal dosage form of this invention can vary, although in preferred preparations the components are present in amounts lying within certain ranges.

A solution for delivering all components simultaneously to the buccal mucosa, is prepared with the following composition:

TABLE VI

Buccal Mucosal Solution

| Components | |
|---|---|
| Ascorbic acid | 0.88% |
| L-lysine hydrochloride | 0.82% |
| Zinc Sulfate | 0.06% |
| Copper Sulfate | 0.09% |
| N-Acetyl-L-cysteine | 0.83% |
| 2-Amino-2-deoxy-D-glucose | 0.52% |
| | USP units/mL |
| Heparin sodium | 2.20 |
| Excipients | |
| Polyvinyl alcohol, sulfated | 1.00% |
| Polyethylene glycol | 0.50% |
| Benzalkonium chloride | 0.004% |

EXAMPLE 6

D. Dermatological Dosage Forms

Dosage forms of the invention for use in the topical treatment of cutaneous manifestations of HSV infections are prepared in a variety of forms including ointments, gels and creams. These preparations optionally include one or more of the following suitable and pharmaceutically acceptable excipients: isopropyl myristate NF, trolamine NF, SD alcohol 40 (20%), white petrolatum USP, lanolin alcohols NF, mineral oil USP, polyvinyl alcohol gel, cetostearyl alcohol NF, lactic acid USP, calcium stearate, dextran, polyoxyl 40 stearate, methylparaben, propylene glycol, sodium lauryl sulfate, polyethylene glycol (PEG) base, synthetic beeswax (B wax), calcium acetate, purified water USP and similar products.

The above excipients serve a variety of functions as carriers, vehicles, diluents, binders, preservatives, buffers, pH adjusters, emulsifiers and other formulating aids and are currently in wide use in dermatological pharmaceutical products manufactured under GMP standards.

The dermatological dosage forms of this invention can be formulated for administration at rates of one unit dosage form daily or one unit dosage form six times daily. A unit dosage form used three to four times per day is preferred.

The amounts of the nine primary components of this dosage form of the invention can vary, although in preferred preparations the components are present in amounts lying within certain ranges.

TABLE VII

Dermatologic Dosage Form

| Components | |
|---|---|
| Ascorbic acid | 1.20% |
| D-α-Tocopherol | 1.62% |
| L-lysine hydrochloride | 1.12% |
| Zinc Sulfate | 0.08% |
| Copper Sulfate | 0.12% |
| N-Acetyl-L-cysteine | 1.13% |
| 2-Amino-2-deoxy-D-glucose | 0.71% |
| Quercetin | 0.36% |
| | USP units/mL |
| Heparin sodium | 3.00 |
| Excipients | |
| Polyvinyl alcohol, sulfated | 1.00% |
| Benzyl alcohol | 5.00% |
| Polyethylene glycol | 0.50% |
| White petrolatum | 45% |

EXAMPLE 7

E. Vaginal Dosage Forms

Dosage forms of the invention for local use in treating female genital manifestations of HSV infections, especially HSV-2, are prepared in dosage forms for vaginal insertion including vaginal suppositories, gels and tablets. These preparations optionally may include one or more of the following suitable and pharmaceutically acceptable excipients, including but not limited to: isopropyl myristate NF, mineral oil USP, stearyl alcohol NF, benzoic acid USP, pegoxyl 7 stearate, methylparaben, propylparaben, propylene glycol, butylated hydroxyanisole, coconut or palm kernel oil triglycerides, polysorbate 60 or polysorbate 8, peglicol 5, PEG-100 stearate and sorbitan monostearate, calcium lactate, hydroxypropyl methylcellulose, polysaccharide carrageenan, corn starch, lactose, calcium lactate, silicon dioxide and purified water USP, among others.

The above excipients serve a variety of functions as carriers, vehicles, diluents, binders, preservatives, buffers, pH adjusters, emulsifiers and other formulating aids and are currently in use in vaginal pharmaceutical products manufactured under GMP standards.

The vaginal dosage form of this invention can be formulated for administration at rates of one unit dosage form daily or one unit dosage form twice daily. A unit dosage form to be used one time per day is preferred.

The amounts of the eight primary components of the vaginal dosage form of this invention can vary, although in preferred preparations the components are present in amounts lying within certain ranges.

TABLE VIII

Vaginal Dosage Form

| Components | |
|---|---|
| Ascorbic acid | 1.04% |
| L-Lysine hydrochloride | 0.97% |
| Zinc Sulfate | 0.07% |
| Copper Sulfate | 0.10% |
| N-Acetyl-L-cysteine | 0.98% |
| 2-Amino-2-deoxy-D-glucose | 0.62% |
| Quercetin | 0.31% |
| | USP units/mL |
| Heparin sodium | 2.60 |
| Excipients | |
| Polyvinyl alcohol, sulfated | 0.05% |
| Mineral oil | 30% |
| White petrolatum | 45% |

Methods of Administration and Types of Utility

The compositions and dosage forms of the invention are useful for treating HSV-1 and HSV-2 infections of epithelial-derived tissues including but not limited to the eye, genitals, and mouth, etc., whether of mucous membrane or dermal origin. The individual formulations consist of orchestrated groups of complementary biofactors that have interlocking antiviral activities. Each functional biofactor has an identifiable and individual antiviral activity which acts against the virus at a different locus of fusion, invasion or replication, which sum with one another to provide the total antiviral activity of the orchestrated formulation: i.e., prevention of virion fusion with the cell to be invaded, interruption of viral DNA replication, improvement of cellular immunomodulation, restoration of endogenous antioxidant potency, etc. however, in some formulations biofactors are incorporated to work not additively, but synergistically, to provide a leveraged therapeutic effect, i.e., although individually $Cu^{2+}$ and ascorbic acid each negatively influence invasive viruses, when combined they create a synergistic anti-viral effect. Still other biofactors may be included which act synergistically with current cytotoxic drugs (i.e., quercetin with acyclovir or with deoxyuridine). As a result, when the invention is used, the chosen array of carefully selected biofactors function in complementarity and the combined anti-viral result is potent and unique. At the same time, toxic side effects, high drug costs and the development of viral resistance (a recognized problem with the use of acyclovir at least) are avoided.

The invention is not designed to replace current therapeusis for HSV. Its clinical use will reduce recurrence rates and the severity of infection, and will reduce reliance upon present drugs. It is designed to create a biological environment in which the opportunity for success with present and future therapies will be increased, the possibility for failure reduced.

As is apparent, both oral dosage forms and topical dosage forms of the invention are described. These dosage forms are designed to provide adequate therapeutic doses of formulation if used alone, or if used in combination, not to exceed appropriate therapeutic levels. This variety of dosage forms and formulations will permit the advising physician great latitude in tailoring for the patient appropriate intensities of treatment for HSV disease at variable clinical levels of severity.

The foregoing is offered primarily for purposes of illustration. It will be readily apparent to those skilled in the art that the proportions, materials, formulation procedures, administration protocols and other parameters of this invention may be further modified or substituted in various ways without departing from the spirit and scope of the invention.

We claim:

1. A unit dosage form for the treatment of herpes simplex and conditions giving rise thereto, said unit dosage form being an ophthalmic ointment or gel comprising as active ingredients:

(a) about 1.3 μg/mL to about 30 μg/mL of ascorbic acid, (b) about 0.01 mg/mL to about 0.2 mg/mL of 2-amino-2-deoxy-D-glucose, (c) about 0.06 μg/mL to about 8.5 μg/mL of zinc sulfate, and (d) about 1.6 μg/mL to about 23 μg/mL of L-lysine hydrochloride.

2. A unit dosage form in accordance with claim 1 further comprising as an active ingredient copper sulfate in a concentration ranging from about 0.4 μg/mL to about 15 μg/mL.

3. A unit dosage form in accordance with claim 1 further comprising as an active ingredient quercetin in a concentration ranging from about 0.12 μg/mL to about 2.75 μg/mL.

4. A unit dosage form in accordance with claim 1 further comprising as an active ingredient heparin sodium in a concentration ranging from about 0.6 units/mL to about 8 units/mL.

5. A unit dosage form in accordance with claim 1 further comprising as active ingredients quercetin in a concentration ranging from about 0.12 μg/mL to about 2.75 μg/mL and heparin sodium in a concentration ranging from about 0.6 units/mL to about 8 units/mL.

6. A unit dosage form in accordance with claim 1 further comprising as active ingredients quercetin in a concentration ranging from about 0.12 μg/mL to about 2.75 μg/mL, heparin sodium in a concentration ranging from about 0.6 units/mL to about 8 units/mL, and N-acetyl-L-cysteine in a concentration ranging from about 0.02 mg/mL to about 0.5 mg/mL.

* * * * *